US006410273B1

(12) United States Patent
Crouzet et al.

(10) Patent No.: US 6,410,273 B1
(45) Date of Patent: Jun. 25, 2002

(54) METHOD FOR PRODUCING METHYLATED DNA

(75) Inventors: Joël Crouzet, Sceaux; Béatrice Cameron, Paris, both of (FR)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/202,314

(22) PCT Filed: Jun. 24, 1997

(86) PCT No.: PCT/FR97/01116
§ 371 (c)(1),
(2), (4) Date: Nov. 12, 1998

(87) PCT Pub. No.: WO98/01540
PCT Pub. Date: Jan. 15, 1998

(30) Foreign Application Priority Data

Jul. 4, 1996 (FR) ............................................ 96 08327

(51) Int. Cl.⁷ ...................... C12N 15/00; C12N 15/63; C12P 19/34; C07H 21/02; C07H 21/04
(52) U.S. Cl. ................... 435/91.1; 435/320.1; 435/455; 536/23.1; 536/23.7
(58) Field of Search .............................. 435/320.1, 455, 435/91.1; 536/23.1, 23.5, 23.7; 514/1, 44

(56) References Cited

U.S. PATENT DOCUMENTS

| | | | |
|---|---|---|---|
| 5,405,760 A | * | 4/1995 | Raleigh et al. ........... 435/91.53 |
| 5,470,740 A | | 11/1995 | Longo et al. |
| 5,491,060 A | * | 2/1996 | Stein et al. ...................... 435/6 |
| 5,580,859 A | | 12/1996 | Felgner et al. ................. 514/44 |
| 5,589,466 A | | 12/1996 | Felgner et al. ................. 514/44 |
| 5,693,622 A | | 12/1997 | Wolff et al. .................... 514/44 |
| 6,060,245 A | | 5/2000 | Sorge et al. ...................... 435/6 |
| 6,153,597 A | | 11/2000 | Blanch et al. ................. 514/44 |
| 6,156,338 A | | 12/2000 | Vacus et al. ................. 424/450 |
| 6,171,612 B1 | | 1/2001 | Byk et al. .................... 424/450 |
| 6,172,048 B1 | | 1/2001 | Behr et al. .................... 514/44 |
| 6,200,956 B1 | | 3/2001 | Scherman et al. ............ 514/13 |

FOREIGN PATENT DOCUMENTS

| | | |
|---|---|---|
| EP | 412 676 | 2/1991 |
| WO | 95/16045 | 6/1995 |
| WO | 96/02555 | 2/1996 |

OTHER PUBLICATIONS

Mastrangelo et al., Seminars in Oncology, vol. 23, No. 1, p. 4–21, Feb. 1996.*
Verma et al., Nature, vol. 389, p. 239–242, Sep. 1997.*
Eck et al., Goodman & Gilman's The Pharmacological Basis of Therapeutics, Ninth Edition, McGraw–Hill, New York, Chapter 5, p. 77–101, 1996.*
Tollefsbol et al., The Journal of Biological Chemistry, vol. 270(31), p. 18543–18550, Aug. 1995.*
Orkin et al., Report and Recommendations of the Panel to Assess the NIH Investment in Research on Gene Therapy, Dec. 1995.*
Krieg et al., Nature, vol. 374, p. 546–549, Apr. 1995.*
Krieg et al. *Nature* (1995) 374,546.
Klinman et al. (1997) *J. Immunol.*, 158, p3635.
Pasquini et al. (1999) *Gene Therapy*, 6, p1448.
McLachlan et al. (2000) *Gene Therapy*, 7, p384.
Blum et al. (1989) *J of Bacteriol*, 171, p538.
Hamilton et al. (1989) *J. Bacteriol*, 171, p4617.
Slater et al. (1993) *J. Bacteriol*, 175, p4260.
Metcalf et al. (1994) *Gene*, 138, p1.
Time Magazine article entitled "Fixing the Genes" (Jan. 11, 1999, pp. 68–73).
Excerpt from 1999 Promega catalogue, p. 5.43.
Krieg et al., CpG motifs in bacterial DNA trigger direct B–cell activation, Nature 374, 546–549 (1995).
Pisetsky, Immunologic Consequences of Nucleic Acid Therapy, Antisense Research & Development 5:219–225 (1995).
Klinman et al., CpG motifs present in bacterial DNA rapidly induce lymphocytes to secrete interleukin 6, interleukin 12, and interferon gamma, Proc. Natl. Acad. Sci. 93, 2879–2883 (1996).
Messina et al., Stimulation of In Vitro Murine Lymphocyte Proliferation By Bacterial DNA, The Journal of Immunology 147(6), 1759–1765 (1991).
Pisetsky et al., Immunological Properties of Bacterial DNAa, Animals of the New York Academy of Sciences 772, 152–163 (1995).

* cited by examiner

*Primary Examiner*—Deborah J. R. Clark
*Assistant Examiner*—Shin-Lin Chen
(74) *Attorney, Agent, or Firm*—Wiley Rein & Fielding LLP

(57) ABSTRACT

The invention discloses the preparation of DNA, in particular plasmid DNA. More particularly it concerns the production of bacterial plasmid DNA to be used in gene therapy, in the form of plasmid, minicircle supercoiled, loose or linear.

15 Claims, 3 Drawing Sheets

METHOD FOR PRODUCING METHYLATED DNA

Figure 1:
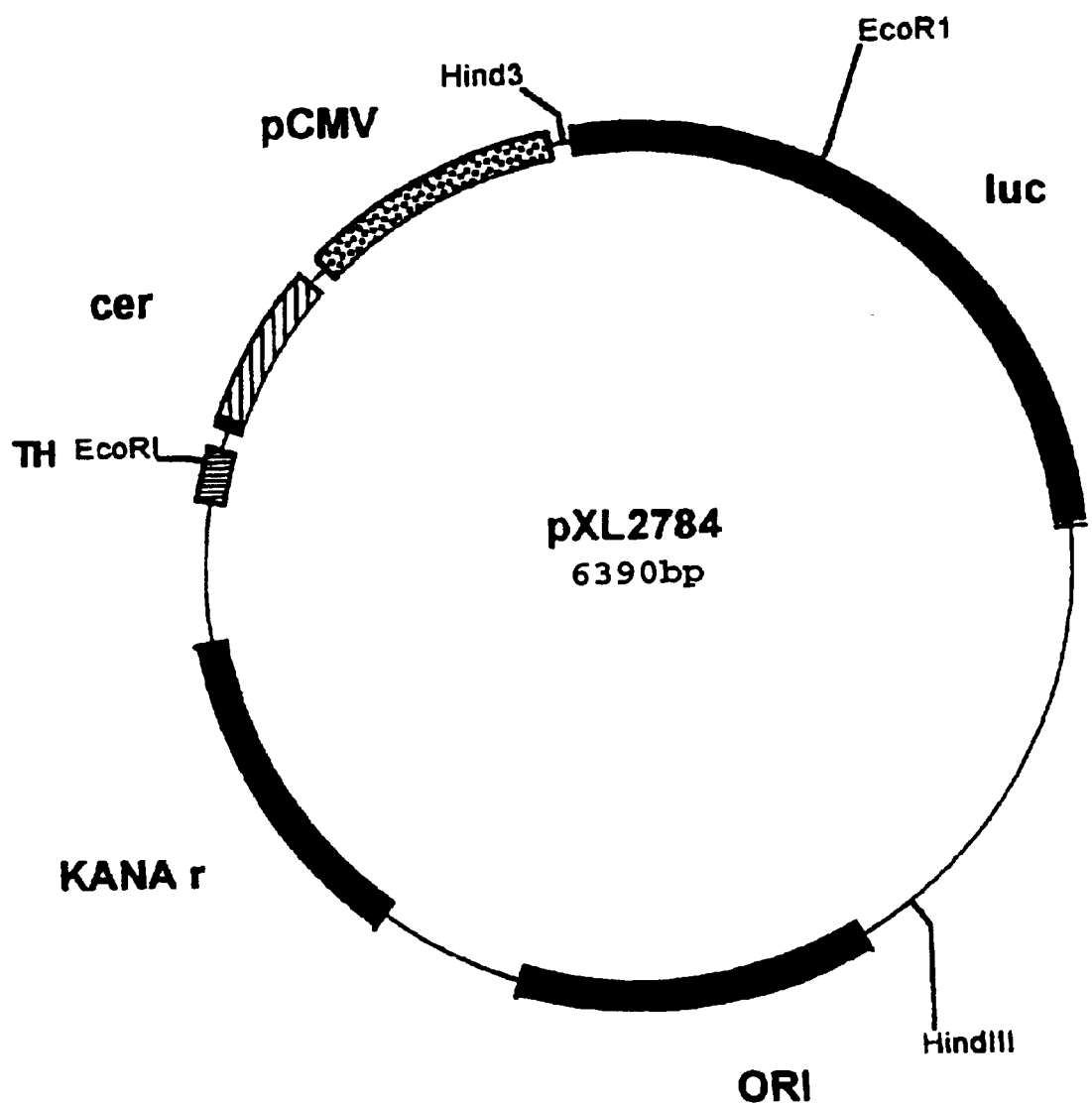

This application claims priority to international application PCT/FR97/01116, filed Jun. 24, 1997.

The present invention relates to the preparation of DNA, in particular plasmid DNA. It relates more especially to the production of bacterial plasmid DNA which can be used in gene therapy, in plasmid, supercoiled or relaxed minicircle or linear form, and whose immunogenic properties are reduced or even eliminated. The invention also relates to microorganisms which can be used for the production of DNA, as well as to pharmaceutical compositions.

Gene therapy consists in correcting a deficiency or an abnormality by introducing genetic information into the affected cell or organ. This information may be introduced either in vitro into a cell extracted from the organ and then reinjected into the body, or in vivo, directly into the target tissue. Being a negatively charged, high molecular weight molecule, DNA has difficulties in passing spontaneously through the phospholipid cell membranes. Various vectors are hence used in order to permit gene transfer: viral vectors on the one hand, natural or synthetic chemical and/or biochemical vectors on the other hand. Viral vectors (retroviruses, adenoviruses, adeno-associated viruses, etc.) are very effective, in particular for passing through the membranes, but present a number of risks, such as pathogenicity, recombination, replication, immunogenicity, etc. Chemical and/or biochemical vectors enable these risks to be avoided (for reviews, see Behr, 1993, Cotten and Wagner, 1993). They are, for example, cations (calcium phosphate, DEAE-dextran, etc.) which act by forming precipitates with DNA, which precipitates can then be "phagocytosed" by the cells. They can also be liposomes in which the DNA is incorporated and which fuse with the plasma membrane. Synthetic gene transfer vectors are generally cationic lipids or polymers which complex DNA and form therewith a particle carrying positive surface charges. These particles are capable of interacting with the negative charges of the cell membrane and then of crossing the latter. As examples of such vectors, dioctadecylamidoglycylspermine (DOGS, Transfectam™) or N-[1-(2,3-dioleyloxy)propyl]-N,N,N-trimethylammonium chloride (DOTMA, Lipofectin™) may be mentioned. Chimeric proteins have also been developed: they consist of a polycationic portion which condenses the DNA, linked to a ligand which binds to a membrane receptor and gives rise to the complex in the cells by endocytosis. It is thus theoretically possible to "target" a tissue or certain cell populations in order to improve the in vivo bioavailability of the transferred gene.

The plasmids currently used in gene therapy generally carry (i) an origin of replication, (ii) a marker gene such as a gene for resistance to an antibiotic (kanamycin, ampicillin, etc.) and (iii) one or more transgenes with sequences necessary for their expression (enhancer(s), promoter(s), polyadenylation sequences, etc.). This type of plasmid is, for example, currently used in gene therapy in the context of clinical trials such as the treatment of melanoma, Nabel et al., 1992, or in the context of experimental studies.

The use of plasmid DNA in gene therapy creates, however, a number of problems.

In particular, it entails the possibility of producing large amounts of DNA of pharmacological purity. In effect, in these gene therapy techniques, the medicament consists of the DNA itself, and it is essential to be able to manufacture, in appropriate amounts, DNAs having suitable properties for therapeutic use in man. In this connection, various methods of production and/or purification have been described in the prior art, enabling the quality of the plasmid DNA to be improved (PCT/FR95/01468; FR96 03519).

Moreover, the use of DNA carrying genes for resistance to antibiotics or functional origins of replication can also have some drawbacks, linked, in particular, to their dissemination in the body. Various approaches have also been developed to limit these drawbacks (PCT/FR96/00274, FR95 10825).

Another drawback of the plasmid DNAs used hitherto lies in their origin. They are, in effect, molecules produced essentially in prokaryotic organisms (bacteria) or lower eukaryotic organisms (yeasts), which potentially possess motifs which are immunogenic in man. The immunological properties of DNA are still relatively unknown. Bacterial DNA in mice leads i) to the synthesis of antibodies that recognize double-stranded and single-stranded bacterial DNA, which has made immunization possible, but do not react with mammalian double-stranded DNA, and ii) to the stimulation of macrophage and cytokine production (D. Pisetsky "The Immunologic Properties of DNA", J. Immunol. 156 (1996) 1). The DNA macromolecule is thus said to be immunogenic. Moreover, a macromolecule can also lead to a stimulation of the immune system without being immunogenic (for example, foreign body leading to a cell-mediated immune response). The first evidence suggesting that bacterial DNA leads to an immune response was described by Pisetsky et al. (1991 J. Immunol. 147 p.1759). They showed that the DNA of three bacterial species can stimulate the proliferation of mouse lymphocytes, whereas the DNA extracted from three animal species does not lead to this stimulation. Then, Yamamoto et al. (1992 Microbiol. Immunol. 36 p.983) observed that the bacterial DNA of six species leads in the spleen cells of BALB/c mice to an increase in "natural killer" NK activity and to the induction of interferon production. However, the DNA extracted from ten vertebrate species does not lead to any of these responses. In addition, Krieg et al. reported in 1995 (Nature vol.374 p.546) that a genomic DNA fragment of E. coli induces in vitro the proliferation of murine B cells and the secretion of IgM immunoglobulins, whereas this same bacterial DNA treated in vitro with a CpG methylase does not induce such a response. Krieg et al. also showed that, in the presence of unmethylated DNA, interferon-$\gamma$ is produced, and acts as a factor which costimulates the differentiation of B cells by modulating the production of IL-6 by the B cells (Krieg et al. 1996 J. Immunol. 156 p.558). Furthermore, an oligonucleotide possessing an unmethylated CpG motif and flanked at the 5' end by 2 purines and at the 3' end by 2 pyrimidines leads in vivo to a coordinated secretion of interleukins IL-6 and IL-12 and of interferons-$\gamma$ by NK cells (IFN-$\gamma$), B cells (IL-6 and IL-12) and CD4$^+$ T lymphocytes (IL-6 and IFN-$\gamma$) (Krieg et al. 1996 Proc. Natl. Acad. Sci. USA 93 p.2879).

The plasmid DNA used to date in gene therapy is essentially produced in prokaryotic cells, and hence displays a methylation profile comparable to that of bacterial genomic DNA. It has, in addition, been demonstrated that plasmid DNA which has been injected into muscle or into the liver, and then extracted, retains the prokaryotic methylation profile (Wolf et al. 1992 Hum. Mol. Genet. 1 p.363; Malone et al. 1995 J. Biol. Chem. 269 p.29903). As a result, the bacterial plasmid DNA used has considerable potential for stimulation of the immune system.

Hence it would be especially advantageous to be able to have at one's disposal plasmid DNA having immunological properties which are reduced or even eliminated. It would also be especially advantageous to be able to have at one's disposal a method that enables plasmid DNAs of this type to be produced on a scale which is compatible with an industrial utilization.

The present invention provides a solution to these problems. The Applicant directed its attention, in effect, to the immunogenic properties of bacterial DNA. The Applicant has now developed a method which enables pharmaceutical grade plasmid DNAs, potentially lacking undesirable immunogenic effects, to be produced. The Applicant also showed that the methylation of some residues of of DNA enabled the immunogenic potential of plasmid DNAs to be reduced without affecting their capacity to transfect cells and to express a nucleic acid of interest therein.

One aspect of the invention is to prepare DNAs, in particular plasmid DNAs, of therapeutic quality. According to another aspect, the present invention relates to the use in gene therapy of plasmid DNA methylated on the cytosines of the dinucleotides 5'-CG-3'. A third aspect of the invention relates to pharmaceutical compositions comprising methylated plasmid DNAs. The invention also relates to a method for the in vivo methylation of DNA by expression of a methylase. The invention, in other aspects, relates to expression cassettes, host microorganisms which can be used for methylation, the preparation of therapeutic compositions and methods of gene transfer.

A first subject of the invention hence relates to a method for the production of DNA which can be used in gene therapy, characterized in that the said DNA is produced in a cell containing a cassette for the expression of a DNA methyltransferase that enables the cytosine residues of the dinucleotides 5'-CG-3' to be methylated.

Hence the present invention relates to the production of DNA, in particular plasmid DNA, which is methylated on the cytosine residues of the dinucleotides 5'-CG-3'.

The methylation of plasmid DNA in vitro is documented in the literature (Adams et al. 1992 FEBS Letters 309 p.97; Doerfler 1994 FEBS Letters 344 p.251; Komura et al. 1995 Biochim. Biophys. Acta 1260 p.73). However, this mode of methylation cannot be envisaged for the industrial production of a plasmid which would be used in gene therapy. A method of plasmid DNA production must, in effect, enable large and homogeneous amounts of plasmids to be produced reproducibly, and this DNA to be purified by methods which are acceptable for pharmaceutical application. It is quite clear that a DNA methylated in vitro perhaps more or less relaxed from batch to batch (Doerfler 1994 FEBS Letters 344 p.251), and that the amounts produced are limited.

The present invention now shows that it is possible to methylate a plasmid of interest directly during production, by coexpressing in the host cell the gene coding for a methylase. The present invention also shows that, according to this method, large and homogeneous amounts of methylated plasmid can be produced, and that the methylated plasmid DNA can be purified according to methods which are already described. The Applicant has also demonstrated, advantageously, that the plasmid DNA thus methylated retains the capacity to transfect target cells and, where appropriate, to replicate therein. It is especially noteworthy that the Applicant has also demonstrated that the plasmid DNA thus methylated can, in vivo, express nucleic acids of interest.

Numerous studies back up, in effect, the idea that hypermethylation is correlated with the inhibition or inactivation of promoters, and that actively transcribed promoters are often hypo- or unmethylated. Thus, in the case of viral promoters, if the E2A late promoter of the adenovirus type 2 genome is fully methylated on the dinucleotides 5'-CG-3' in HE1 transformed hamster cells and unmethylated in HE2 transformed hamster cells, the E2A gene is silent in HE1 and transcribed in HE2 (W. Doerfler 1995 Curr. Top. Microbiol. Immunol. 197 p.209). Another example is described by Kohn et al. (1994 Proc. Natl. Acad. Sci. USA 91 p.2567), who show that the absence of expression from the LTR retroviral vector transduced in haematopoietic stems cells is associated with methylation in vivo. The inhibition of the expression of a reporter gene, under the control of a viral promoter, when this gene is introduced in transient transfection by a plasmid methylated in vitro has also been demonstrated (Adams et al. 1992 FEBS Letters 309 p.97; Doerfler 1994 FEBS Letters 344 p.251; Komura et al. 1995 Biochim. Biophys. Acta 1260 p.73). Moreover, Razin et al. (loc. cit.) have shown that the promoter of the herpes simplex type I gene coding for thymidine kinase and that of the mouse gene coding for metallothionein are inactive during transient expression in mouse L cells and murine F9 teratocarcinoma cells if these promoters are methylated on the dinucleotides 5'-CG-3'.

Hence the present invention describes for the first time a method that makes it possible to produce methylated plasmid DNA which is homogeneous and compatible with an industrial utilization, and demonstrates the possibility of using this type of plasmid for the expression of genes in vitro, ex vivo or in vivo, in particular in gene therapy applications.

The method according to the invention may be carried out in various types of cell host. The latter is, in particular, any non-human cell essentially lacking a system for methylation of the cytosines of the dinucleotides 5'-CG-3'. The absence of methylation may be the result of the absence of suitable enzyme activity, due either to an insufficient expression of a corresponding gene or to the absence of the said gene. Prokaryotic or simple eukaryotic cells are preferably used.

Advantageously, the cell host is a bacterium. Among bacteria, *E. coli, B. subtilis,* Streptomyces, Pseudomonas (*P. putida, P. aeruginosa*), *Rhizobium melioti, Agrobacterium tumefaciens, Staphylococcus aureus, Streptomyces pristinaespiralis, Enterococcus faecium* or Clostridium may be mentioned more preferentially. It is also possible to use enterobacteria such as *Salmonella typhimurium, Klebsiella pneumoniae, Enterobacter aerogenes, Erwinia carotovora* or *Serratia marcescens*. Preferentially, the cell host used is a non-pathogenic organism and enables large and homogeneous amounts of plasmid DNA to be produced. As an especially preferred example, *E. coli* is used.

The method of the invention permits DNA of therapeutic quality to be produced.

The DNA can be any linear or circular, single-stranded or double-stranded DNA molecule, replicative or otherwise, integrative or otherwise, in plasmid, supercoiled or relaxed minicircle or linear form. In the text hereinafter, the DNA will also be referred to as GT plasmid DNA or GT plasmid (for plasmid which can be used in gene therapy).

The GT plasmids generally used in gene therapy essentially carry (i) an origin of replication, (ii) one or more nucleic acids of interest (therapeutic gene) with sequences necessary for their expression (enhancer(s), promoter(s), polyadenylation sequences, etc.) and, optionally, (iii) a marker gene.

The choice of the origin of replication is mainly determined by the cell host used for production. It can be an origin of replication originating from a plasmid of the incompatibility group P (for example pRK290) which permits replication in *E. coli* pol A strains. More generally, it can be any origin of replication originating from a plasmid that replicates in prokaryotic or lower eukaryotic cells. This plasmid can be a derivative of pBR322 (Bolivar et al., Gene 2 (1977) 95), a derivative of pUC (viera and Messing, Gene 19 (1982) 259) or other plasmids derived from the same incompatibility group, that is to say from ColE1 or pMB1, for example. These plasmids may be chosen, moreover, from other incompatibility groups that replicate in *Escherichia coli*. Possible plasmids are ones derived from plasmids belonging to the incompatibility groups A, B, FI, FII, FIII, FIV, H1, H11, I1, I12, J, K, L, N, OF, P, Q, T, U, W, X, Y, Z or 9, for example. Other plasmids may also be used, among them plasmids that do not replicate in *E. coli* but in other hosts such as *B. subtilis,* Streptomyces, *P. putida, P. aeruginosa, Rhizobium meliloti, Agrobacterium tumefaciens, Staphylococcus aureus, Streptomyces pristinaespiralis, Enterococcus faecium* or Clostridium. As a preferential choice, the origins of replication originating from plasmids that replicate in *E. coli* are used. According to a particular variant, the origin of replication can be a conditional origin, that is to say one whose activity depends on the presence of factors in trans. The use of this type of origin of replication prevents replication of the plasmid DNA after administration, for example in man (FR95 10825).

Among the marker genes, there may be mentioned a gene for resistance, in particular, to an antibiotic (ampicillin, kanamycin, geneticin, hygromycin, and the like), or any gene conferring on the cell a function it no longer possesses (for example a gene which has been deleted on the chromosome or rendered inactive), the gene on the plasmid re-establishing this function.

According to a particular embodiment, the plasmid DNA contains sequences that enable all the essentially non-therapeutic regions (origin of replication, marker gene, and the like) to be removed after the production phase. An especially advantageous approach for generating this type of molecule (minicircle) has been described in Application PCT/FR96/00274.

The plasmid DNA according to the invention is preferably a double-stranded DNA molecule containing one or more nucleic acids of interest with sequences necessary for their expression. According to a preferred embodiment, a replicative or integrative circular molecule is used. Advantageously, the plasmid DNA contains essentially one or more nucleic acids of interest with sequences necessary for their expression (miniplasmid).

The nucleic acid of interest can be any nucleic acid (cDNA, gDNA, synthetic or semi-synthetic DNA, and the like) whose transcription and, where appropriate, translation in a cell generate products having therapeutic, vaccinal, agricultural or veterinary importance.

Among nucleic acids having therapeutic properties, there may be mentioned, more especially, the genes coding for enzymes, blood derivatives, hormones, lymphokines, namely interleukins, interferons, TNF, and the like (FR 92 03120), growth factors, neurotransmitters or their precursors or synthetic enzymes, trophic factors, namely BDNF, CNTF, NGF, IGF, GMF, aFGF, bFGF, NT3, NT5, and the like; apolipoproteins, namely ApoAI, ApoAIV, ApoE, and the like (FR 93 05125), dystrophin or a minidystrophin (FR 91 11947), tumour-suppressing genes, namely p53, Rb, Rap1A, DCC, k-rev, and the like (FR 93 04745), genes coding for factors involved in coagulation, namely factors VII, VIII, IX, and the like, suicide genes, namely those for thymidine kinase, cytosine deaminase, and the like; or alternatively all or part of a natural or artificial immunoglobulin (Fab, ScFv, and the like), a ligand RNA (WO91/19813), and the like. The therapeutic gene can also be an antisense gene or sequence whose expression in the target cell enables gene expression or the transcription of cellular mRNAs to be controlled. Such sequences can, for example, be transcribed in the target cell into RNAs complementary to cellular mRNAs, and can thus block their translation into protein, according to the technique described in Patent EP 140 308.

The nucleic acid of interest can also be a vaccinating gene, that is to say a gene coding for an antigenic peptide capable of generating an immune response in man or animals, with a view to the production of vaccines. Such antigenic peptides can be, in particular, ones specific to the Epstein-Barr virus, the HIV virus, the hepatitis B virus (EP 185 573) or the pseudorabies virus, or alternatively tumour-specific peptides (EP 259 212).

Generally, in the plasmids, the nucleic acid of therapeutic, vaccinal, agricultural or veterinary importance also contains a transcription promoter region which is functional in the target cell or organism (i.e. mammals, especially man), as well as a region located at the 3' end and which specifies a transcription termination signal and a polyadenylation site. As regards the promoter region, this can be a promoter region naturally responsible for the expression of the gene in question when the promoter region is capable of functioning in the cell or organism in question. Regions of different origin (responsible for the expression of other proteins, or even synthetic regions) are a further possibility. In particular, the promoter regions may be promoter sequences of eukaryotic or viral genes. For example, they can be promoter sequences originating from the genome of the target cell. Among eukaryotic promoters, it is possible to use any promoter or derived sequence that stimulates or represses the transcription of a gene, specifically or otherwise, inducibly or otherwise, strongly or weakly. Possible promoters are, in particular, ubiquitous promoters (HPRT, PGK, α-actin, tubulin, and the like, gene promoter), promoters of intermediate filaments (GFAP, desmin, vimentin, neurofilament, keratin, and the like, gene promoter), promoters of therapeutic genes (for example the MDR, CFTR, factor VIII, ApoAI, and the like, gene promoter), tissue-specific promoters (pyruvate kinase, villin, intestinal fatty acid binding protein, smooth muscle α-actin, and the like, gene promoter) or alternatively promoters that respond to a stimulus (steroid hormone receptor, retinoic acid receptor, and the like). Similarly, the promoter sequences can be ones originating from the genome of a virus, such as, for example, the promoters of the adenovirus E1A and MLP genes, the CMV early promoter or alternatively the RSV or MMTV LTR promoter, and the like. In addition, these promoter regions may be modified by adding activating or regulatory sequences, or sequences permitting a tissue-specific or -preponderant expression.

Moreover, the gene of interest can also contain a signal sequence that directs the product synthesized into the pathways of secretion of the target cell. This signal sequence can be the natural signal sequence of the product synthesized, but it can also be any other functional signal sequence, or an artificial signal sequence.

Depending on the nucleic acid of interest, the methylated plasmid DNAs of the invention can be used for the treatment or prevention of numerous pathologies, including genetic disorders (dystrophy, cystic fibrosis, and the like), neurodegenerative diseases (Alzheimer's, Parkinson's, ALS, and the like), cancer, pathologies associated with coagulation disorders or with dyslipoproteinaemias and pathologies associated with viral infections (hepatitis, AIDS, and the like), or in the agricultural and veterinary fields, and the like. They are especially advantageous for the treatment of pathologies in which a lasting expression without an immunological reaction is desired, in particular in the field of genetic, neurodegenerative and cardiovascular disorders and diseases.

As stated above, the method according to the invention employs a host cell containing a cassette for the expression of a DNA methyltransferase that enables the cytosine residues of the dinucleotides 5'-CG-3' to be methylated.

After DNA synthesis, some purines and pyrimidines are modified chemically, for example by methylation. Thus, 5-methylcytosine or $N^6$-methyladenine participates in the composition of some DNAs. These modifications take place by means of DNA methyltransferases, maintenance or de novo enzymes, which transfer a methyl group from S-adenosyl-L-methionine to adenine or cytosine residues which may be located at specific positions in the sequences. For example, in *E. coli,* two DNA methyltransferases are well known, the dam DNA methyltransferase which methylates adenosine residues within the sequences 5'-GATC-3', and the dcm DNA methyltransferase which methylates the second cytidine residue of the sequences 5'-CCA/TGG-3'. Other DNA methylases have been studied in bacteria, which methylate a residue contained in a restriction enzyme recognition site. For example, the enzyme M. HpaII methylates the second cytosine residue in the sequence 5'-CCGG-3'.

Most simple eukaryotes and most invertebrates contain relatively little 5-methylcytosine and $N^6$-methyladenine. However, the methylation of bases in vertebrates is more extensive and, in this case, 5-methylcytosine is the commonest of the methylated bases. In effect, more than 95 percent of the methyl groups of vertebrate DNA occurs on the C residues of the uncommon dinucleotides 5'-CG-3' (the frequency of 0.8% of 5'-CG-3' in mammalian sequences is very low, although the percentage of GC is 40% on average and an unbiased arrangement would lead to a frequency of 4% of 5'-CG-3'). And more than 50 percent of the collective dinucleotides can be methylated. A variety of evidence suggests that the degree of methylation of some sequences containing the dinucleotide 5'-CG-3' might be a determining factor in mammals in the regulation of the expression of particular genes, inactivation of the X chromosome, oncogenesis (1993 in DNA methylation: Molecular Biology and Biological Significance, Eds Jost and Saluz) and also hereditary disorders (Bates et al. 1994 BioEssays 16 p.277).

The present invention employs a cassette for the expression of a DNA methyltransferase that enables the cytosine residues on the dinucleotides 5'-CG-3' to be methylated. As a result, for the purposes of the present invention, methylated DNA means, more especially, DNA methylated on the cytosine residues of the dinucleotides 5'-CG-3'. Advantageously, the DNA methyltransferase used preferentially methylates the cytosine residues of the dinucleotides 5'-CG-3', that is to say has virtually no effect on adenine residues, or on cytosine residues which are present in a different context from the 5'-CG-3' dinucleotides. Advantageously, methylated plasmid DNA is understood to mean a plasmid DNA in which at least 50% of the cytosine residues of the dinucleotides 5'-CG-3' are methylated. More preferably, at least 80% and advantageously 90% of the said residues are methylated.

The methylation of the plasmid DNA may be verified in various ways. In particular, it may be monitored by digesting the plasmid preparations with restriction enzymes which are unable to cut if the cytosine residue of the dinucleotide 5'-CG-3' contained in the cleavage site is methylated. There may be mentioned, for example, the restriction enzymes HPaII, AatII, BstBI. The methylation may also be determined by chromatography. Thus, the amount of unmethylated plasmid present in the methylated plasmid preparation has been quantified in the following manner: 1% or 5% of unmethylated plasmid completely digested with HpaII is added to the undigested unmethylated plasmid. These samples, together with the methylated plasmid digested with HpaII, are analysed by anion exchange liquid chromatography and detection at 260 nm, which enables the undigested DNA to be separated and quantified from the digested DNA. It is found that the methylated plasmid contains less than 5% of unmethylated plasmid DNA, in other words more than 95% of the plasmid DNA is methylated.

Advantageously, the method of the invention is characterized in that the DNA methyltransferase preferentially methylates the cytosine residues of the dinucleotides 5'-CG-3'.

Advantageously, in the method according to the invention, more than 50% of the cytosine residues of the dinucleotides 5'-CG-3' of the plasmid DNA are methylated. Still more preferably, more than 80%, and especially more than 90%, of the cytosine residues of the dinucleotides 5'-CG-3' of the plasmid DNA are methylated.

Several mammalian DNA methyltransferases that enable the cytosine residues on sequences containing any dinucleotide 5'-CG-3' to be methylated have been characterized and the corresponding genes have been cloned, for example the mouse enzyme (Bestor et al. 1988 J. Mol. Biol. 203 p.971) or the human enzyme (Yen et al. 1992 Nucl. Acids Res. 20 p.2287). These enzymes have a molecular weight of between 135 and 175 kD. They methylate hemimethylated DNA much more rapidly than unmethylated DNA, suggesting that they are maintenance methylases (Smith 1994 Progress in Nucleic Acid Research and Molecular Biology 49 p.65). The homologous enzyme in *E. coli* does not exist. In contrast, the *Spiroplasma methylase* M. SssI methylates exclusively and completely the cytosine residues of any dinucleotide 5'-CG-3' at a comparable rate, irrespective of whether the substrate is hemimethylated or unmethylated (Razin et al. 1992 FEBS Letters 313 p.243; Baker et al. 1993 Biochim. Biophys. Acta 196 p.864). This enzyme was isolated from the strain Spiroplasma sp. MQ1. Its molecular weight is 42 kD and the gene has been cloned and overexpressed in *E. coli* (Razin et al. 1990 Nucl. Acids Res. 18 p.1145 and EP0412676A1 Derwent 91045812).

Preferably, the DNA methyltransferase is chosen from methylase M.SssI, mouse methylase and human methylase. Advantageously, methylase M.SssI is used.

The cassette for the expression of the DNA methyltransferase generally comprises a nucleic acid coding for a DNA methyltransferase that enables the cytosine residues of the dinucleotides 5'-CG-3' to be methylated under the control of a promoter. The promoter used for this purpose can be any promoter which is functional in the chosen host cell. In this connection, it can be a promoter as defined above. In the case of prokaryotic cell hosts, there may be mentioned, more especially, the promoters of the lactose operon (Plac) and of the tryptophan operon (Ptrp), the hybrid promoters Plac/Ptryp, the $P_L$ or $P_R$ promoter of bacteriophage lambda, the tetA gene promoter (in Vectors 1988 p.179 Rodriguez and Denhardt editors), and the like.

In a preferred embodiment, a promoter is used which is different from the one responsible for the expression of the nucleic acid of interest in the plasmid DNA. It is most especially advantageous to use an inducible promoter that enables the expression of the methylase to be controlled. The inducible promoter can be, for example, the promoter of bacteriophage T7 or the Plac promoter.

Advantageously, the expression cassette also contains transcription termination signals (transcription terminators) such as ribosomal terminators.

The cassette for the expression of the DNA methyltransferase can be carried by a replicative vector or can be integrated in the genome of the host cell.

In the case of a replicative vector, it is advantageous to use a vector which is compatible with the GT plasmid, that is to say one capable of coexisting in the same cell. Two different plasmids can replicate in the same cell if the control of the replication of each plasmid is different. Thus, compatible plasmids belong to two incompatibility groups. Now, there are approximately 30 incompatibility groups of plasmids that replicate in enterobacteria (Maas et al. 1988 Microbiol. Rev. 52 p.375). As a result, there are numerous possibilities for replicating two plasmids in the same cell, and several examples are described in the literature. There may be mentioned, for example, the coreplication of plasmids derived from ColE1 with plasmids having as their replicon R6K or p15A or RSF1010 or RK2; there may also be mentioned the coreplication of plasmids derived from RK2 with plasmids derived from R6K or RSF1010 or pSa or ColE1 (in Vectors 1988 p.287 Rodriguez and Denhardt editors). This list is not limiting, and yet further examples are described in Vectors 1988 p.287 Rodriguez and Denhardt editors. Advantageously, the replicative vector used has a different copy number in the host cell from that of the GT plasmid. Thus, the vector carrying the gene coding for the methylase, whose expression can be inducible, is a low copy number vector (derived, for example, from pACYC184 or RK2), whereas the GT plasmid is a high copy number plasmid (derived from ColE1). It is also possible to clone into the GT plasmid a sequence that enables a triple-helical sequence to be formed with a suitable oligonucleotide, so that the GT plasmid can be separated from the other plasmid by an affinity purification.

The cassette for the expression of the DNA methyltransferase may also be integrated in the genome of the host cell. The integration may be carried out by homologous recombination, provided that the expression cassette is flanked by adjacent fragments of a non-essential gene of the host's genome and cloned into a plasmid which cannot replicate in the host in question. This plasmid can be i) a derivative of ColE1 in an *E. coli* polA$^{ts}$ strain (Gutterson et al. 1983 Proc. Natl. Acad. Sci. USA 80 p.4894); ii) a temperature-sensitive derivative of pSC101 in any *E. coli* strain (S. Kushner et al. 1989 J. Bacteriol. 171 p.4617); iii) a suicide vector such as M13mp10 in *E. coli* sup$^+$ strains (Blum et al. 1989 J. Bacteriol. 171 p.538) or alternatively iv) a plasmid containing only the origin g of R6K in any *E. coli* strain lacking the pir gene (Filutowicz et al. 1994 Prog. in Nucleic Acid Res. and Mol. Biol. 48 p.239).

The expression cassette may be introduced into the host cell before, after or at the same time as the plasmid DNA. In the case of an integrative cassette, it is generally introduced beforehand, and the cells containing the said cassette are selected and used for the production of the plasmid DNA.

One particular aspect of the invention is to express the gene coding for methylase M. SssI in bacterial cells (in particular *E. coli*) containing a GT plasmid. As shown in the examples, the said plasmid is then methylated on the cytosines of the dinucleotides 5'-CG-3'. More specifically, the GT plasmid is transformed into an *E. coli* mcrA mcrB D(mcrC-mrr) strain already containing a plasmid carrying the gene coding for methylase M. SssI and compatible with the GT plasmid. During the growth of the bacterium, both plasmids coexist, replicate and are methylated (Gotschlich et al. J. Bacteriol. 173 p.5793).

The plasmid DNA or the expression cassette may be introduced into the host cell by any technique known to a person skilled in the art (transformation, transfection, conjugation, electroporation, pulsing, precipitation, and the like). The transformation may be performed, in particular, by the $CaCl_2$ transformation technique (Dagert and Ehrlich, Gene 6 (1979) 23), or the one developed by Hanahan et al. (J. Mol. Biol. 166 (1983) 557) or any technique derived from the latter (Maniatis et al., 1989), as well as by electrotransformation (Wirth et al., Mol. Gen. Genet. 216 (1989) 175) or using TSB (transformation and storage buffer; Chung et al. 1988 Nucleic Acids Res. 16 p.3580). See also the General Techniques of Molecular Biology below.

The methylated plasmid DNA according to the invention can then be purified by any technique known to a person skilled in the art (precipitations, chromatographic runs, centrifugations, dialysis, and the like). In the particular case of the use of a replicative vector for the expression of the methyltransferase, the GT plasmid must, in addition, be separated from the said vector. Various techniques may be used, based on the size or mass differences of the two plasmids, or on the digestion of the vector at restriction sites present only in the vector and not in the GT plasmid. An especially advantageous method of purification is based on the the affinity between a specific sequence present on the GT plasmid and an immobilized oligonucleotide. This triple-helix purification has been described in detail in Applications FR96 03519 and FR94 15162, which are incorporated herein by reference.

An especially advantageous result of the invention is that the plasmid DNA methylated under the conditions of the invention leads to as good an expression of the gene under the control of the promoter as is obtained with the same plasmid DNA unmethylated. This methylated plasmid DNA should not give rise to the immune stimulation associated with bacterial DNAs, and hence possesses a definite advantage for use in non-viral gene therapy.

The methylated plasmid DNAs according to the invention may be used in any vaccination or gene and cell therapy application, for the transfer of a gene to a body, a tissue or a given cell. In particular, they may be used for direct administration in vivo, or for the modification of cells in vitro or ex vivo, with a view to their implantation in a patient. In this connection, the molecules according to the invention may be used as they are (in the form of naked DNA), or in combination with various synthetic or natural chemical and/or biochemical vectors. Possible vectors include, in particular, cations (calcium phosphate, DEAE-dextran, etc.) which act by forming precipitates with the DNA, which precipitates can be "phagocytosed" by the cells. Other possible vectors are liposomes in which the DNA molecule is incorporated and which fuse with the plasma membrane. Synthetic gene transfer vectors are generally cationic lipids or polymers which complex DNA and form therewith a particle carrying positive surface charges. These particles are capable of interacting with the negative charges of the cell membrane and then of crossing the latter. As examples of such vectors, DOGS (Transfectam™) or DOTMA (Lipofectin™) may be mentioned. Chimeric proteins have also been developed: they consist of a polycationic portion which condenses the DNA, linked to a ligand which binds to a membrane receptor and gives rise to the complex in the cells by endocytosis. The DNA molecules according to the invention may also be used for the transfer of genes to cells by physical transfection techniques such as bombardment, electroporation, and the like. In addition, prior to their therapeutic use, the molecules of the invention can optionally be linearized, for example by enzymatic cleavage.

In this connection, another subject of the present invention relates to any pharmaceutical composition comprising a methylated plasmid DNA as defined above. This DNA may be naked or combined with a chemical and/or biochemical transfection vector. The pharmaceutical compositions according to the invention may be formulated with a view to topical, oral, parenteral, intranasal, intravenous, intramuscular, subcutaneous, intraocular, transdermal, and the like, administration. Preferably, the DNA molecule is used in an injectable form or a form to be applied. It may be mixed with any vehicle which is pharmaceutically acceptable for an injectable formulation, in particular for direct injection at the site to be treated. Such vehicles can be, in particular, isotonic sterile solutions, or dry, in particular lyophilized compositions which, on addition of sterilized water or of physiological saline, as appropriate, enable injectable solutions to be made up. Examples include, in particular, Tris or PBS buffers diluted in glucose or sodium chloride. Direct injection of the nucleic acid into the affected region of the patient is advantageous, since it enables the therapeutic effect to be concentrated in the tissues concerned. The doses of nucleic acid used may be adjusted in accordance with various parameters, and in particular in accordance with the gene, the vector, the mode of administration used, the pathology in question or the desired treatment period.

The present invention will be described more completely by means of the examples which follow, which are to be regarded as illustrative and non-limiting.

LEGEND TO THE FIGURES

FIG. 1. Map of the plasmid pXL2784

Figure 2:
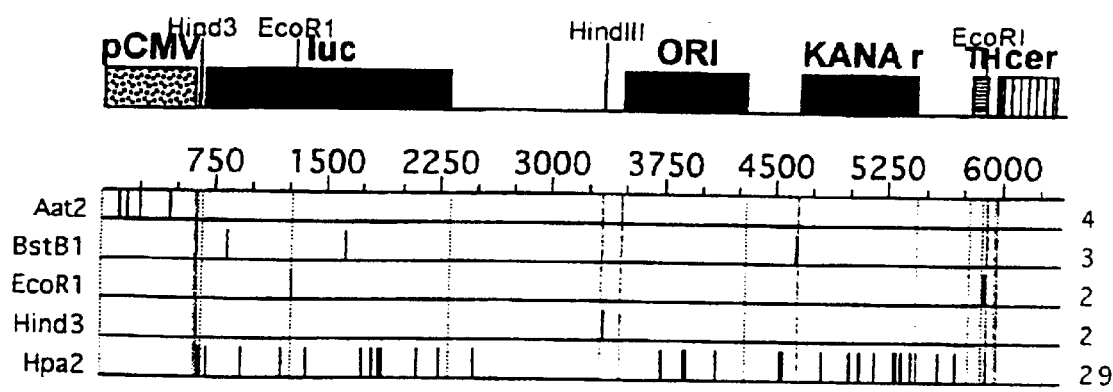

FIG. 2. Restriction map of the plasmid pXL2784

Figure 3:
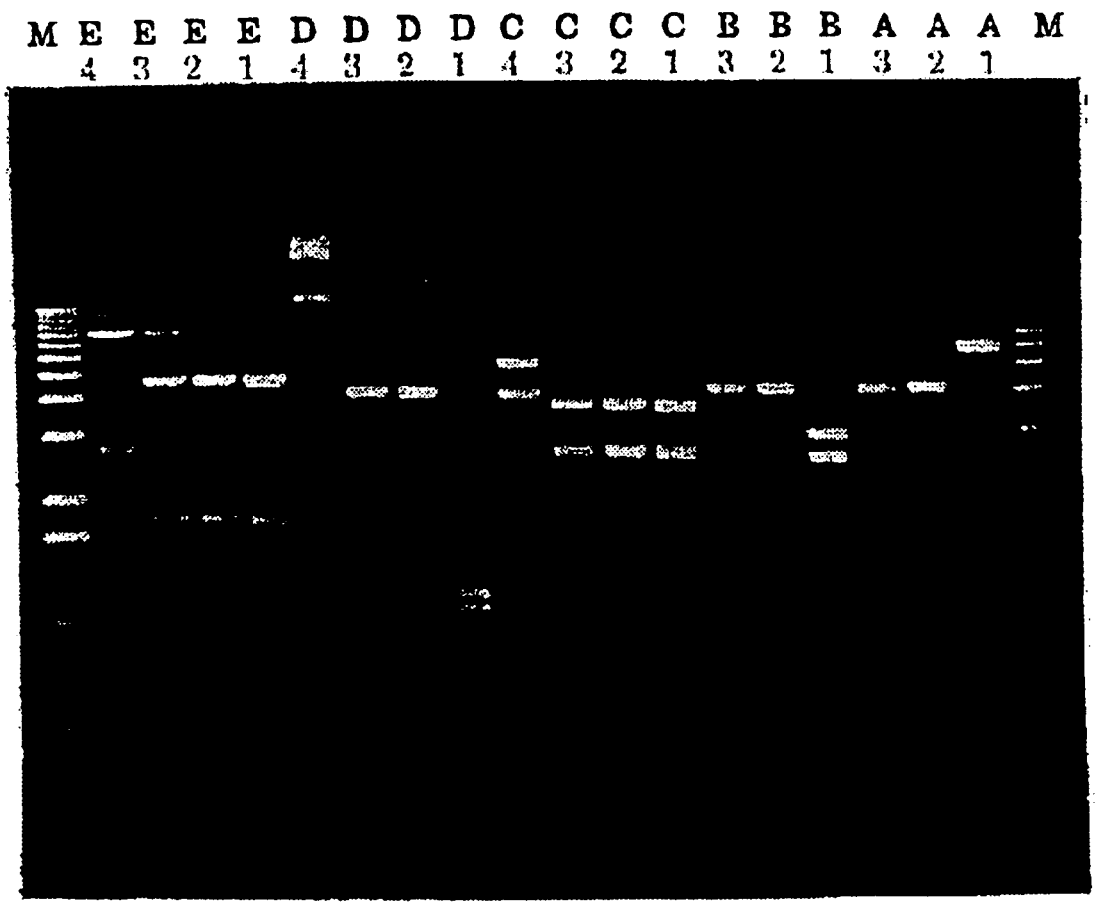

FIG. 3. Digestion profile of the plasmids 1-pXL2784, 2-methylated pXL2784, 3-methylated pXL2784+ methylated pAIT2 and 4-methylated pAIT2, digested with the enzymes A-AatII, B-BstBI, C-HindIII, D-HpaII, E-EcoRI (M is the 1 kb ladder molecular weight marker).

GENERAL TECHNIQUES OF CLONING AND OF MOLECULAR BIOLOGY

The standard methods of molecular biology, such as centrifugation of plasmid DNA in a caesium chloride-ethidium bromide gradient, digestion with restriction enzymes, gel electrophoresis, electroelution of DNA fragments from agarose gels, transformation in *E. coli*, precipitation of nucleic acids, and the like, are described in the literature (Maniatis et al., 1989, Ausubel et al., 1987). Nucleotide sequences were determined by the chain termination method according to the protocol already presented (Ausubel et al., 1987).

Restriction enzymes were supplied by New England Biolabs (Biolabs), Bethesda Research Laboratories (BRL) or Amersham Ltd (Amersham).

For the ligations, the DNA fragments are separated according to their size on 0.7% agarose or 8% acrylamide gels, purified by electrophoresis and then electroelution, extracted with phenol, precipitated with ethanol and then incubated in 50 mM Tris-HCl buffer pH 7.4, 10 MM $MgCl_2$, 10 mM DTT, 2 mM ATP, in the presence of phage T4 DNA ligase (Biolabs). Oligonucleotides are synthesized using phosphoramidite chemistry, the latter derivatives being protected at the β-position by a cyanoethyl group (Sinha et al., 1984, Giles 1985), with an Applied Biosystems 394 DNA/RNA Synthesizer automatic DNA synthesizer using the manufacturer's recommendations.

LB and 2XTY culture media are used for the bacteriology part (Maniatis et al., 1989).

Plasmid DNAs are also purified according to the alkaline lysis technique (Maniatis et al., 1989).

EXAMPLES

Example 1

Description of the GT Plasmid

Numerous cassettes for eukaryotic expression which are carried by plasmids that are replicative in the *E. coli* bacterium are known to a person skilled in the art. These cassettes can express reporter genes such as the *E. coli* gene coding for β-galactosidase, or the transposon Tn9 chloramphenicol acetyltransferase, or luciferase, or genes which are of interest in gene therapy. These cassettes contain a promoter which can be viral or eukaryotic. These expression systems can be tissue-specific and/or inducible, or can alternatively be expressed ubiquitously. The cassette used in this example comprises the luc gene, coding for *Photinus pyralis* luciferase, and the pCMV promoter, the human cytomegalovirus intermediate promoter/enhancer. The luc gene possesses 4.78% of dinucleotides 5'-CG-3', and the pCMV viral promoter 5%. Hence these percentages are high relative to the low frequency of 0.8% of 5'-CG-3' in mammalian sequences. In the presence of a methylase (such as methylase M. SssI or the CpG methylases which are endogenous to mammals), the pCMV promoter and the luc gene can hence be highly methylated.

This expression cassette was cloned into the plasmid pXL2784, which is replicative in *E. coli*, the map of which is presented in FIG. 1. The plasmid is 6390 bp in size and contains 5.8% of dinucleotides 5'-CG-3'. Plasmid pXL2784 was constructed from the vector pXL2675 (2.513 kb), the minimal replicon of ColE1 originating from pBluescript (ORI) and having as selectable marker the transposon Tn5 gene coding for resistance to kanamycin. Plasmid pXL2784 also contains a TH sequence $(GAA)_{17}$ which can bind to an oligomer $(CTT)_n$ where n=1 to 17, to generate locally a triple-helical structure and permit an affinity purification. Plasmid pXL2784 possesses the cer locus (382 bp) originating from ColE1; the cer locus contains a site-specific sequence for the recombinases XerC/XerD, and leads to the resolution of plasmid dimers (Summers et al. 1988 EMBO J. 7 p.851). The transgene cloned into this plasmid pXL2784 is an expression cassette (3.3 kb) for the luc gene coding for *Photinus pyralis* luciferase (originating from Promega pGL2 basic), under the control of the human cytomegalovirus PCMV enhancer/promoter (originating from Invitrogen pcDNA3).

Example 2

Construction of a Cassette for the Expression of a DNA Methyltransferase

This example describes the structure of a cassette for the expression of the Spiroplasma sp. MQ1 methylase M. SssI. It is understood that the same principle may be applied to the construction of a cassette for the expression of any other enzyme according to the invention.

The expression cassette used comprises the gene encoding the Spiroplasma sp. MQ1 methylase M. SssI, which is expressed under the control of the Plac promoter. Thus, in the presence of IPTG (isopropyl β-D-thiogalactoside), the methylase is synthesized and active (Gotschlich et al. 1991 J. Bacteriol. 173 p.5793).

This cassette is present in the plasmid pAIT2, which has as its replicon pACYC184 and carries, in addition, the Tn903 transposon gene coding for resistance to lividomycin, permitting the selection of the transformed host cells.

Example 3

Production of pXL2784 Plasmid DNA Methylated at the Cytosine Residues of the Dinucleotides 5'-CG-3'

Plasmid pXL2784 is methylated on the cytosines of all the dinucleotides 5'-CG-3' with the Spiroplasma sp. MQ1 methylase M. SssI. The mode of methylation according to the invention utilizes this enzyme, and the plasmid is methylated during production in the bacterium.

To this end, *E. coli* strain ER 1821, whose genotype is F⁻ 1⁻endA1 thi1 supE44 mcrA5 D(mrr-hsdRMS-mcrB)1-::IS10, and carrying plasmid pAIT2, is transformed by the TSB (transformation and storage buffer; Chung et al. 1988 Nucleic Acids Res. 16 p.3580) method with plasmid pXL2784. The transformants are selected on LB medium containing 50 mg/l kanamycin and 100 mg/l lividomycin, in order to select the pXL2784 which carries the transposon Tn5 gene coding for resistance to kanamycin and the pAIT2 carries the transposon Tn903 gene coding for resistance to lividomycin. When an ER1821, pAIT2, pXL2784 transformant is cultured in LB medium with 50 mg/l kanamycin+ 100 mg/l lividomycin+2.5 mM IPTG at 37° C. for 15 hours, the plasmid DNA extracted is methylated.

The methylation is verified by digesting the plasmid preparations with the restriction enzymes HpaII, AatII and BstBI. The integrity and the presence of the two plasmids are verified by digesting these preparations with the restriction enzymes HindIII and EcoRI, see FIG. 2. The restriction enzymes HpaII, AatII and BstBI are three enzymes which are unable to cut if the cytosine residue of the dinucleotide 5'-CG-3' contained in the cleavage site is methylated. In the pCMV promoter, four AatII recognition sites are localized; in the luc gene, two BstBI recognition sites and eleven HpaII recognition sites are mapped; the latter enzyme cutting plasmid pXL2784 into 30 fragments. In the photograph of the ethidium bromide-stained agarose gel (FIG. 2), it is seen that, with the methylated plasmid preparation pAIT2+ pXL2784 or with the methylated plasmid preparation pXL2784 purified by affinity chromatography (see Example 4), no digestion takes place with the enzymes HpaII, AatII and BstBI, whereas digestions with the enzymes HindIII and EcoRI do indeed lead to the profile which is expected from the restriction map. Controlled digestions of plasmid pXL2784 with the enzymes HpaII, AatII and BstBI afford the profile which is expected from the restriction map.

These results demonstrate that the plasmid DNA extracted is methylated on the cytosine residues of the dinucleotide 5'-CG-3'. These results show, in addition, that the methylation affects more than 90% of these cytosines.

Example 4

Use of Methylated Plasmids for the Transfer of Genetic Material

This example demonstrates that the methylated plasmid DNA according to the invention retains its capacity to transfect cells, to replicate therein and to express a gene of interest therein.

A Protocol for preparation of the solutions used for transfection

Two groups of plasmids are used for comparative studies:
a) pXL2784,
b) methylated pXL2784.

The methylated plasmid pXL2784 is obtained in the form of a mixture with plasmid pAIT2 which has effected its methylation after bacterial cotransformation. A fractionation by affinity chromatography was carried out in order to purify the plasmid of interest, and the technique used is described in Application No. FR 94 15162. A step of dialysis against 0.15 M NaCl may be carried out in order to remove the buffer which constitutes the elution phase of the column.

When plasmid pXL2784 is used as reference, it is purified according to the same protocol as the one described above.

In this example, the DNA is vectored by a cationic lipid, RPR120535A, belonging to a series described in Patent Application No. FR 95 13490. It is understood that any other chemical or biochemical transfer vector may be used.

The transfection solutions are prepared from a mixture of equal volumes of DNA at a concentration of 30 μg/ml and 90 μM aqueous solution of cationic lipid RPR 120535; the cationic lipid/DNA ratio is hence 3 nanomoles cationic lipid/μg DNA. After homogenization with a vortex mixer and incubation for at least 15 minutes at room temperature, the DNA/lipofectant solutions are distributed in the proportion of 4.8% (v/v) final in wells in which the cells have been washed with protein-free (serum-free) medium and replaced for growth to continue during the period of transfection in serum-free medium.

B Transfection protocol

Samples of 1×10⁵ cells [NIH3T3 (mouse fibroblasts) and HeLa (human uterine carcinoma)] in an exponential growth phase on 2 cm² (500 μl of serum-free medium/well) are treated with 25 μl of transfection solution, which corresponds to the provision of 0.375 μg of DNA/1×10⁵ cells. After incubation for 2 hours at 37° C. under 5% $CO_2$ in a humid atmosphere, the growth medium is supplemented with foetal calf serum at a concentration of 8% final (v/v).

At 40 hours post-transfection, the cells are washed with PBS and lysed with a buffer containing 1% Triton X-100 and 2 mM DTT. The luciferase activity expressed is assayed by light emission [RLU=relative light unit] in the presence of luciferin, coenzyme A and ATP for 10 seconds, and recorded in terms of the mg of proteins extracted by the lysis buffer.

C Results

The results obtained according to the conditions described above appear in the following table.

| | Cell | | | |
| --- | --- | --- | --- | --- |
| | NIH 3T3 Cells | | HeLa Cells | |
| Plasmid | pXL2784 | pXL2784CH3 | pXL2784 | pXL2784CH3 |
| purified by affinity chromatography and dialysed | 2.0 × $10^{10}$ +/− 4% | 2.2 × $10^{10}$ +/− 10% | 3.1 × $10^8$ +/− 15% | 1.7 × $10^8$ +/− 11% |
| | 2.3 × $10^{10}$ +/− 21% | 3.1 × $10^{10}$ +/− 10% | 3.8 × $10^8$ +/− 14% | 2.4 × $10^8$ +/− 7% |

Enzyme activity in RLU/10 seconds/mg protein (coefficient of variation % [3 transfection experiments per result])

Bearing in mind the coefficients of variation obtained for this type of experiment, we can conclude that there are no significant differences regarding the expression of the two plasmids used under the same transfection conditions. Furthermore, the luciferase activity obtained is of the same order of magnitude for both of the purification steps in question.

What is claimed is:

1. A method for the production of a methylated DNA selected from the group consisting of a plasmid DNA and a minicircle, wherein the method comprises transforming a prokaryotic cell with the DNA to be methylated and an expression cassette comprising a nucleic acid encoding a bacterial DNA methyltransferase, wherein the expression cassette is introduced into the prokaryotic cell before, after, or at the same time as the DNA to be methylated, culturing the transformed prokaryotic cell under conditions that permit expression of the bacterial DNA methyltransferase, whereby cytosine residues of 5'-CG-3' dinucleotides of the DNA to be methylated are methylated, and purifying the methylated DNA from the prokaryotic cell.

2. The method according to claim 1, wherein the prokaryotic cell is a bacterium.

3. The method according to claim 2, wherein the bacterium is *Escherichia coli*.

4. The method according to claim 1, wherein the expression cassette is on a replicative vector.

5. The method according to claim 1, wherein the expression cassette is integrated into the genome of the prokaryotic cell.

6. The method according to claim 1, wherein the nucleic acid encoding the bacterial DNA methyltransferase is under the control of a promoter.

7. The method according to claim 6, wherein the promoter is an inducible promoter.

8. The method according to claim 1, wherein the DNA methyltransferase preferentially methylates the cytosine residues of the dinucleotides 5'-CG-3'.

9. The method according to claim 8, wherein the DNA methyltransferase is methylase M.SssI.

10. The method according to claim 1, wherein more than 50% of cytosine residues of 5'-CG-3' dinucleotides of the DNA are methylated.

11. The method according to claim 1, wherein more than 80% of cytosine residues of 5'-CG-3' dinucleotides of the DNA are methylated.

12. The method according to claim 1, wherein more than 90% of cytosine residues of 5'-CG-3' dinucleotides of the DNA are methylated.

13. The method according to claim 1, wherein the methylated DNA is a plasmid.

14. The method according to claim 1, wherein the methylated DNA comprises a nucleic acid encoding a mammalian gene product.

15. The method according to claim 1, wherein the methylated DNA is a minicircle.

* * * * *